(12) United States Patent
Graham (10) Patent No.: US 6,359,278 B1
(45) Date of Patent: Mar. 19, 2002

(54) OPTICAL STABILIZATION OF TEMPERATURE EFFECTS ON AN INFRARED GAS ANALYZER

(75) Inventor: James E. Graham, Brookfield, WI (US)

(73) Assignee: GE Marquette Medical Systems, Inc., Milwaukee, WI (US)

( * ) Notice: Subject to any disclaimer, the term of this patent is extended or adjusted under 35 U.S.C. 154(b) by 0 days.

(21) Appl. No.: 09/474,496

(22) Filed: Dec. 29, 1999

(51) Int. Cl.$^7$ .................................................. G01J 5/02
(52) U.S. Cl. ..................... 250/343; 250/346; 250/339.09
(58) Field of Search .......................... 250/343, 346, 250/347, 339.04, 339.03, 339.09, 339.13

(56) References Cited

U.S. PATENT DOCUMENTS 4,008,394 A * 2/1977 Risgin et al. ............... 250/345
4,692,621 A * 9/1987 Passaro et al. ............. 250/343
5,585,635 A   12/1996 Graham ..................... 250/343

* cited by examiner

Primary Examiner—Georgia Epps
Assistant Examiner—Mohammed Hasan
(74) Attorney, Agent, or Firm—Foley & Lardner; Peter J. Vogel; Michael A. Della Penna (57) ABSTRACT

A method of stabilizing temperature effects on a gas analyzer includes transmitting infrared energy through a plurality of cells in a reference cell drum to a sensor in the gas analyzer. The plurality of cells include at least one cell containing a reference gas and at least one cell containing an air reference. The method also includes interposing a filter in at least one of the plurality of cells in the reference cell drum, wherein energy from the infrared beam is reduced. The method further includes rotating the reference cell drum such that the infrared energy fully passes through each of the plurality of cells for a limited period of time such that the sensor generates a substantial sine wave signal.

20 Claims, 6 Drawing Sheets

OPTICAL STABILIZATION OF TEMPERATURE EFFECTS ON AN INFRARED GAS ANALYZER

BACKGROUND OF THE INVENTION

The present invention relates generally to the field of gas analyzers. More particularly, the present invention relates to a technique for optical stabilization of temperature effects on an infrared gas analyzer.

Infrared (IR) gas analyzers typically include an infrared energy source and an infrared sensor. Disposed between the infrared energy source and the infrared sensor is a cell containing a gas mixture to be analyzed. A filter is generally carried on a rotatable wheel such that multiple filters can be rotated into position between the infrared energy source and infrared sensor. Infrared energy passes through the sample and is reduced by the presence of any gas that absorbs the infrared energy. Selectively imposing filters in the path of the beam of infrared energy changes the wavelength band of the infrared energy. Typically, each filter passes only radiation at a narrow band corresponding to a characteristic absorption wavelength band of a particular gas of interest. As such, through use of an infrared filter that is selected for each gas to be monitored in the gas sample, only infrared energy that can be absorbed by that gas is allowed to pass through the filter to be detected by the sensor.

Figure 1:
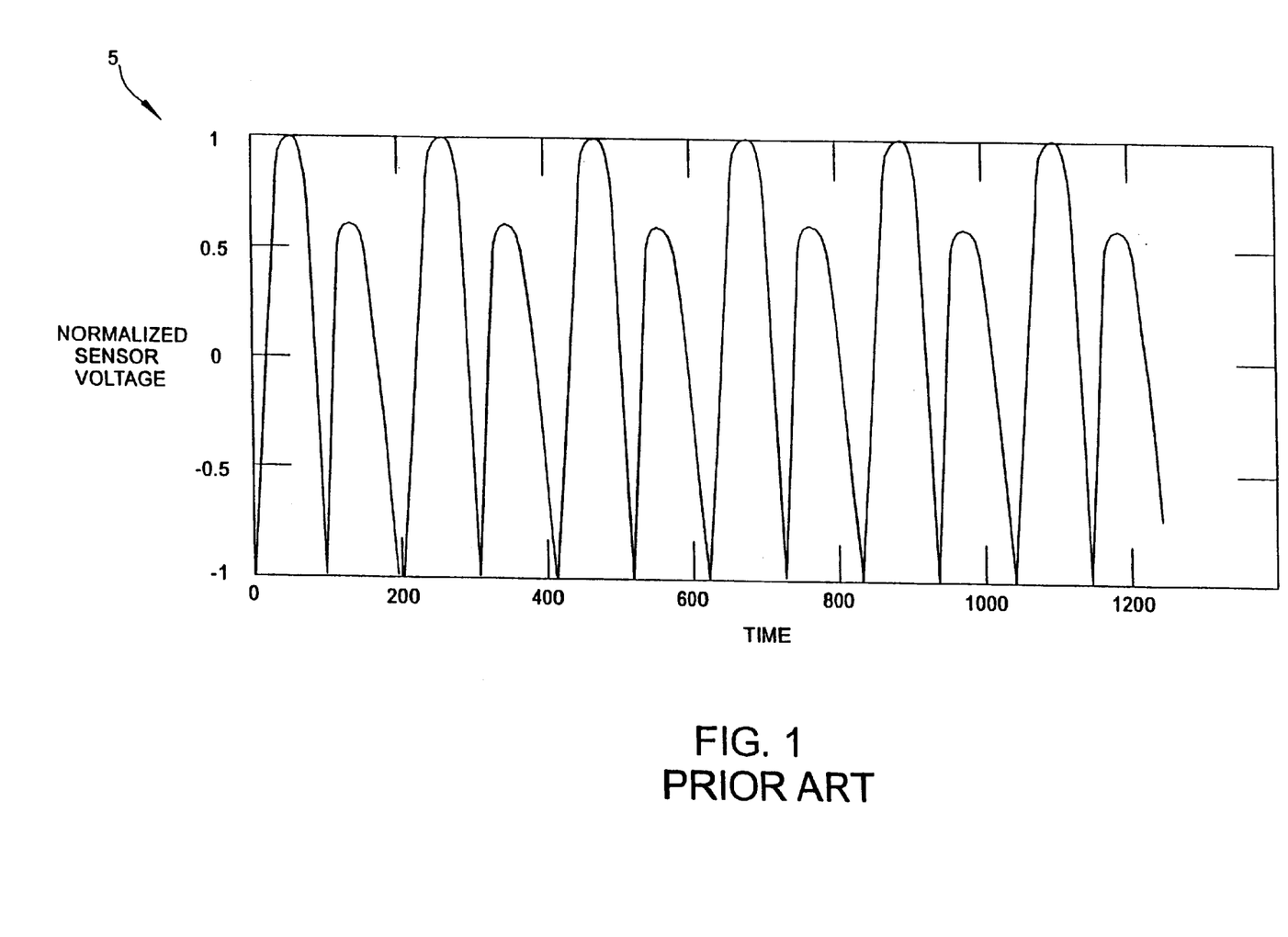
FIG. 1 is a graph illustrating sensor energy to voltage transforms in a sensor of a conventional gas analyzer.

In most IR gas analyzers, there is the need for some form of calibrating reference for the sensor. Conventional calibrating references include chopped dual beam, rotating filters or any other method that produces a varying optical energy signal on the sensor. FIG. 1 shows a graph 5 depicting a typical electrical output of a sensor in a conventional IR gas analyzer, where the low sensor data points (located at the −1 level) represent the voltage measured by the sensor when the filter wheel or chopper is positioned at a dark time (i.e., when all of the IR energy from the IR source is blocked such that the sensor is dark). All measurements are referenced to this point. There is also a reference gas or reference filter that represents a constant attenuation of the IR source energy. These smaller peaks (represented by the 0.6 levels on graph 5), allow for the calibration of the larger peaks that have been (or will be) attenuated by the unknown gas to be measured. By subtracting the dark time from these two peak readings and taking the ratio of the known reference peak to the unknown gas peak, conventional gas analyzers obtain an absolute reading that is representative of the gas amount being measured.

FIG. 1 also shows the sensor signal square wave or "flat top" output. This output is typical of a dual path chopped or negative gas filter type gas analyzer. When the chopper or filter is in alignment with the IR source and sensor, the energy on the sensor is maximum and remains there until the chopper or filter goes out of alignment. The impingement of the maximum energy on the sensor during the alignment period causes the flat top on the signal wave form. This square wave in combination with the difference in peak levels with respect to the same level of the dark time means that, in order to maintain the electronic signal without distortion, the buffer amplifier must pass all frequency from DC to the $3^{rd}$, $5^{th}$ and possibly higher (e.g., $7^{th}$) harmonic of the fundamental. Thus, filtering the sensor noise now requires a balance in distortion and noise.

Ideally, in order to use conventional methods for determining gas amounts, the sensor should be linear. In practice, however, the best infrared sensors (in terms of cost versus speed versus sensitivity) are nonlinear. Nonlinear sensors used in gas analyzers are error prone in relative measurements due to the changing temperature of the sampling environment. To reduce the errors caused by the changing temperature and complex data signals, IR type gas analyzers typically use expensive sensor coolers and sampling environment heaters to reduce the effects of sensor data error.

Thus, there is a need to reduce gas reading errors in gas analyzers without using expensive heaters and coolers that are slow to come to temperature. Further, there is a need to use non-linear sensors in gas analyzers without the data measurement errors which result from changes in environmental temperature. Even further, there is a need to stabilize measurements which are typically unstable by simplifying the sensor data wave signal.

BRIEF SUMMARY OF THE INVENTION

One embodiment of the invention relates to a method of stabilizing temperature effects on a gas analyzer. The method includes transmitting infrared energy through a plurality of cells in a reference cell drum to a sensor in the gas analyzer. The plurality of cells include at least one cell containing a reference gas and at least one cell containing an air reference. The method also includes interposing a filter between the bulb and the sensor in at least one of the plurality of cells in the reference cell drum, wherein energy from the infrared beam is reduced. The method further includes rotating the reference cell drum such that the beam of infrared energy fully passes through each of the plurality of cells for a limited period of time such that the sensor generates a substantial sine wave signal.

Another embodiment of the invention relates to a gas analyzer including a source which emits infrared energy, a sensor which detects infrared energy emitted from the source, a reference cell drum interposed between the source and the sensor, and at least one filter. The reference cell drum includes a plurality of cells through which the infrared energy passes from the source to the sensor. The plurality of cells includes at least one cell containing a reference gas and at least one cell containing an air reference. The reference cell drum is configured to rotate such that the infrared energy fully passes through each of the plurality of cells for a limited period of time such that the sensor generates a substantial sine wave signal. The at least one filter is located within the at least one cell containing an air reference. The at least one filter provides broad spectrum attenuation to reduce the infrared energy passing through the at least one cell containing an air reference.

Another embodiment of the invention relates to a gas analyzer which stabilizes temperature effects without using heaters and coolers. The gas analyzer includes means for transmitting infrared energy through a plurality of cells in a reference cell drum to a sensor. The cells include at least one cell containing a reference gas and at least one cell containing an air reference. The gas analyzer also includes means for filtering infrared energy passing through the at least one cell in the reference cell drum containing an air reference and means for rotating the reference cell drum such that the infrared energy fully passes through each of the plurality of cells for a limited period of time such that the sensor generates a substantial sine wave signal.

Other principle features and advantages of the present invention will become apparent to those skilled in the art upon review of the following drawings, the detailed description, and the appended claims.

BRIEF DESCRIPTION OF THE DRAWINGS

The invention will become more fully understood from the following detailed description, taken in conjunction with the accompanying drawings, wherein like reference numerals denote like elements, in which.

DETAILED DESCRIPTION OF THE PREFERRED EMBODIMENTS

Figure 2:
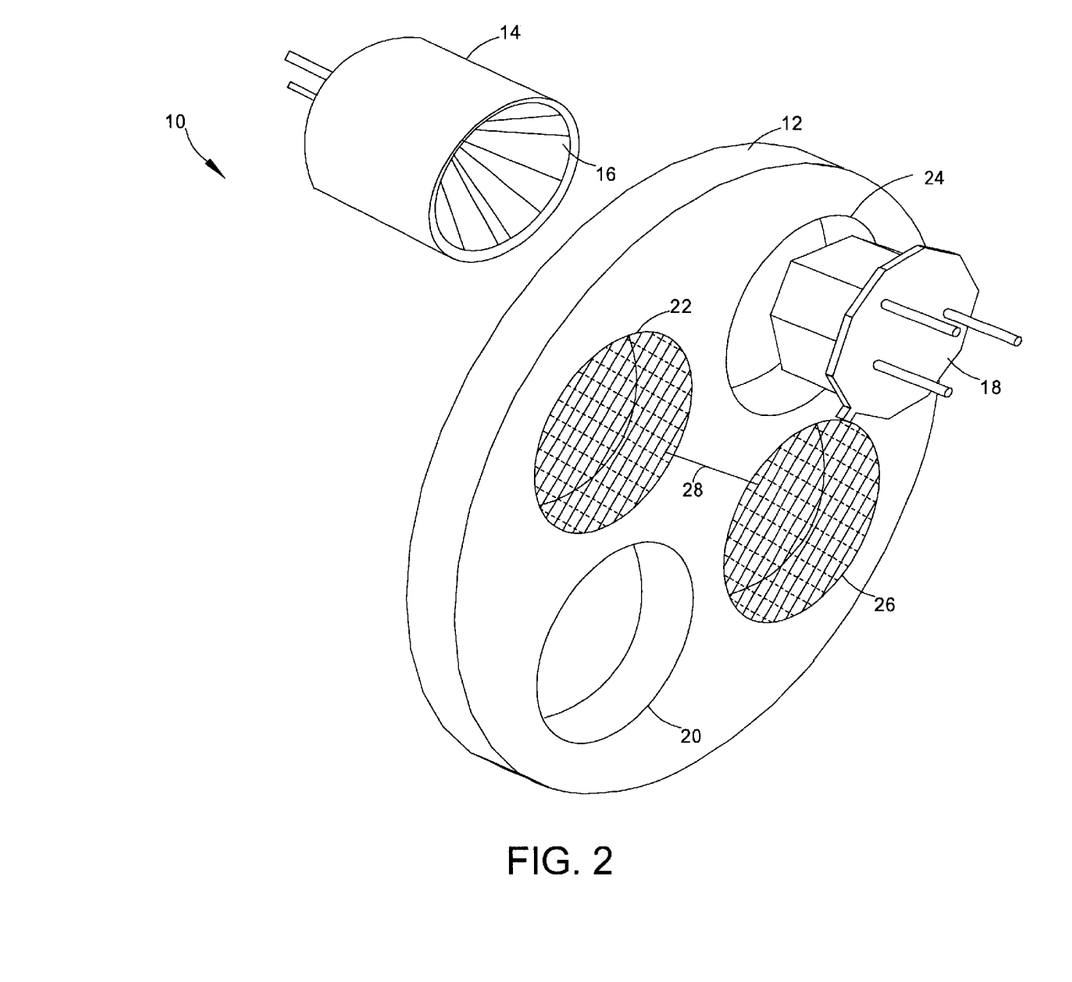
FIG. 2 is a perspective, exploded view of a portion of a gas analyzer including a reference cell drum, an infrared source, and an infrared sensor.

Referring now to the drawings and first to FIG. 2, a portion 10 of a gas analyzer includes a reference cell drum 12, a reflector body 14, a bulb 16, and a sensor 18. Reference cell drum 12 includes cells 20, 22, 24, and 26. Cells 20 and 24 contain a reference gas. Cells 22 and 26 contain air and include a filter 28. In a preferred embodiment, filter 28 is a neutral density optical attenuator.

Reflector body 14 is a cylindrical component housing bulb 16 and having one open end. The interior of reflector body 14 includes tapered walls which are reflective to aid in directing light from bulb 16 out the open end of reflector body 14. Bulb 16 is an infrared energy source, such as, a 5v flashlight bulb which emits a beam of infrared energy. Sensor 18 is any of a variety of gas analyzer sensors and is positioned on one side of reference cell drum 12 opposite reflector body 14. As depicted in FIG. 2, reference cell 24 is currently located between reflector body 14 and sensor 18. However, in operation, reference cell drum 12 is rotatable such that cells 20, 22, 24, and 26 pass one after the other between reflector body 14 and sensor 18 as drum 12 rotates. Infrared energy from bulb 16 passes through each of cells 20, 22, 24, and 26 as reference cell drum 12 rotates. The full spectrum (that the sensor filters can pass) of the infrared source energy will pass through reference cells 20 and 24 and impinge on sensor 18 when cells 20 and 24 are aligned with sensor 18.

Figure 3:
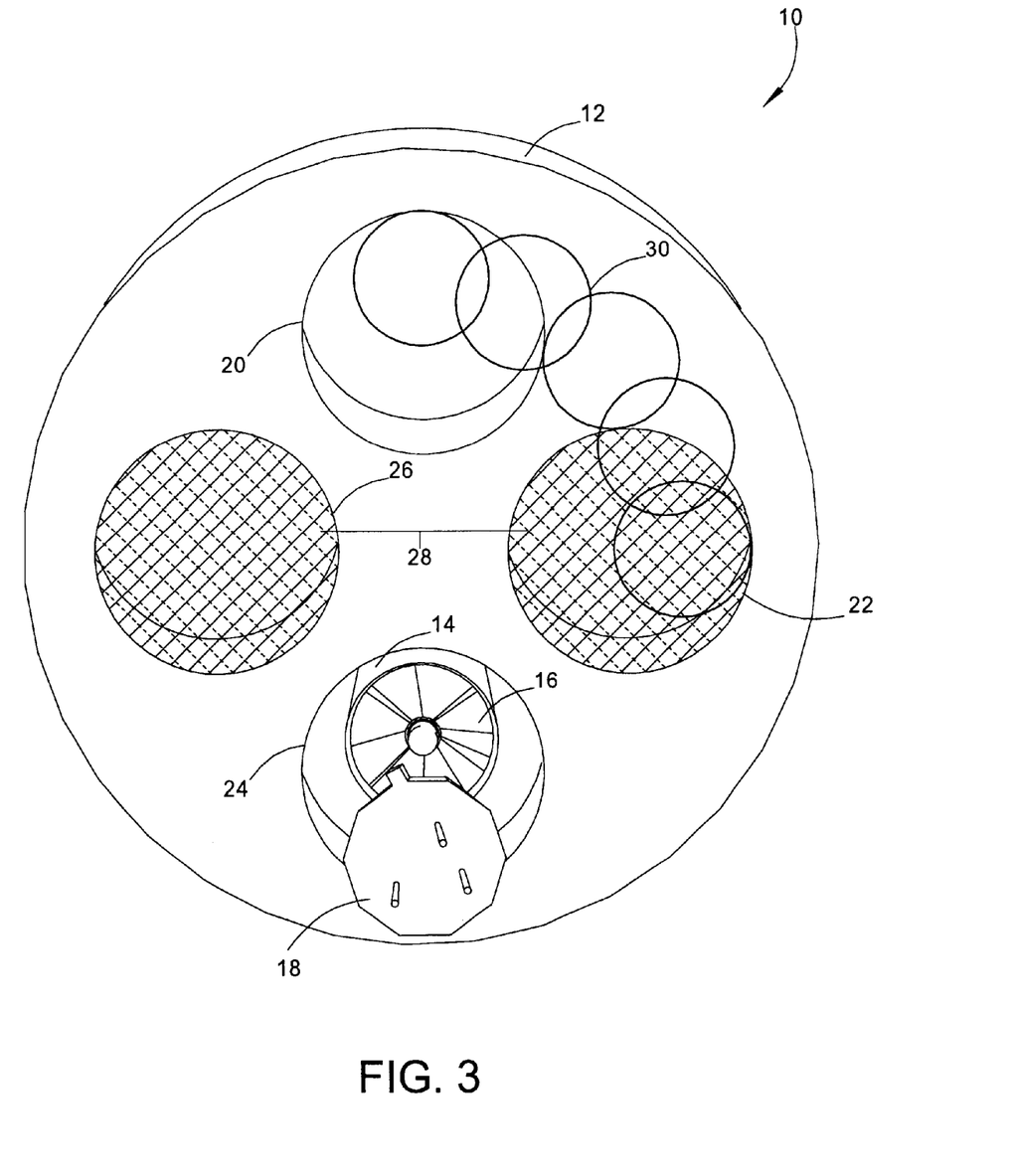
FIG. 3 is a bottom view of the portion of the gas analyzer of FIG. 2 which depicts a series of optical transmittance path rings superimposed on the reference cell drum.

FIG. 3 illustrates a bottom view of portion 10 including five (5) circles 30 which are not part of portion 10 but depict an exemplary path of optical sensor 18 relative to reference cell drum 12 as the drum rotates. Circles 30 also illustrate the path that the infrared beam from bulb 16 will travel across reference cell drum 12. One circle at the top of FIG. 3 is completely aligned or "full on" with cell 20, which contains a reference gas, the next circle in the clockwise direction shows the sensor only halfway aligned "half on" cell 20, and the next circle in the clockwise direction is just out of line with or "full off" cell 20. This third circle, where the sensor 18 is completely out of line with any of cells 20, 22, 24, and 26, represents the "dark time" of the sensor. The cycle repeats in reverse to the last circle that is back to complete alignment or "full on" with cell 22, which contains air and filter 28. As the drum rotates at a constant speed, the "full on" time and the "full off" time does not last long. As such, the time that the full infrared beam is detected by sensor 18 is limited, thereby removing the flat tops of the detected signal wave and generating a near sine wave. Ideally, a perfect sine wave would be preferred but, for ease of manufacture and lower cost, an offset beam through a circle (as shown in FIG. 3) is used to simplify the sensor data wave signal.

Figure 4:
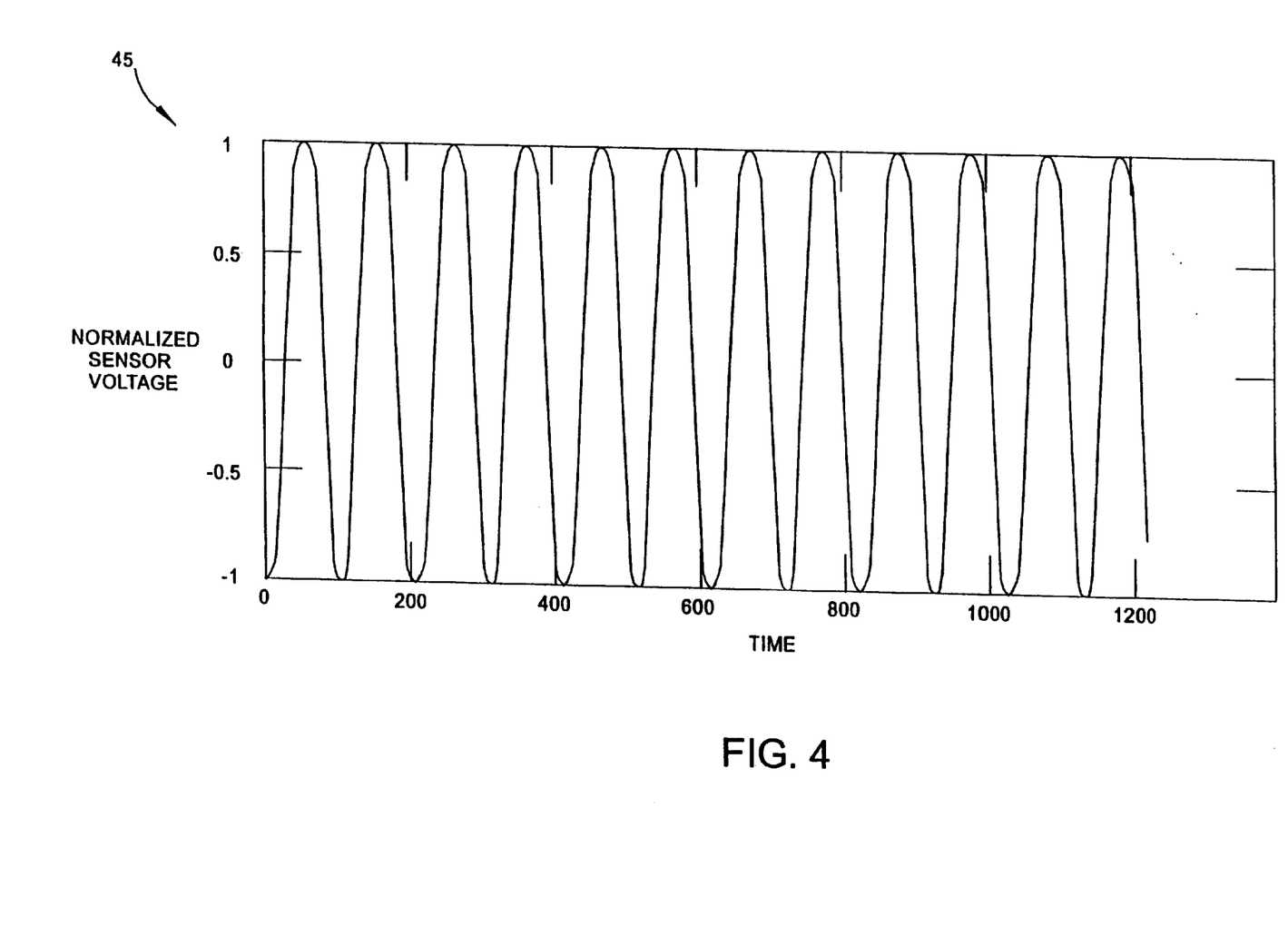
FIG. 4 is a graph illustrating sensor energy to voltage transforms of the sensor of the gas analyzer of FIG. 2.

As reference cell drum 12 turns from a gas reference (e.g., cell 20) to an air reference (e.g., cell 22), the energy on sensor 18 remains near constant from one peak to the next. This constant energy is accomplished by the use of a neutral density filter, filter 28, on the air reference cell (e.g., cell 22). Filter 28 acts as a broad spectrum attenuator, reducing total energy. If the reference gas and neutral density filter are matched, the end result is that the peaks of the signal sensed by sensor 18 will all have the same amplitude, as illustrated by a graph 45 in FIG. 4. A comparison between the signal peaks of graph 45 versus the signal peaks of graph 5 shows that the flat tops of the peaks have been substantially eliminated. A perfect match cannot be accomplished over the range of sample gas to be measured, but getting close makes removal of the remaining error a smaller and more straight forward correction.

Figure 5:
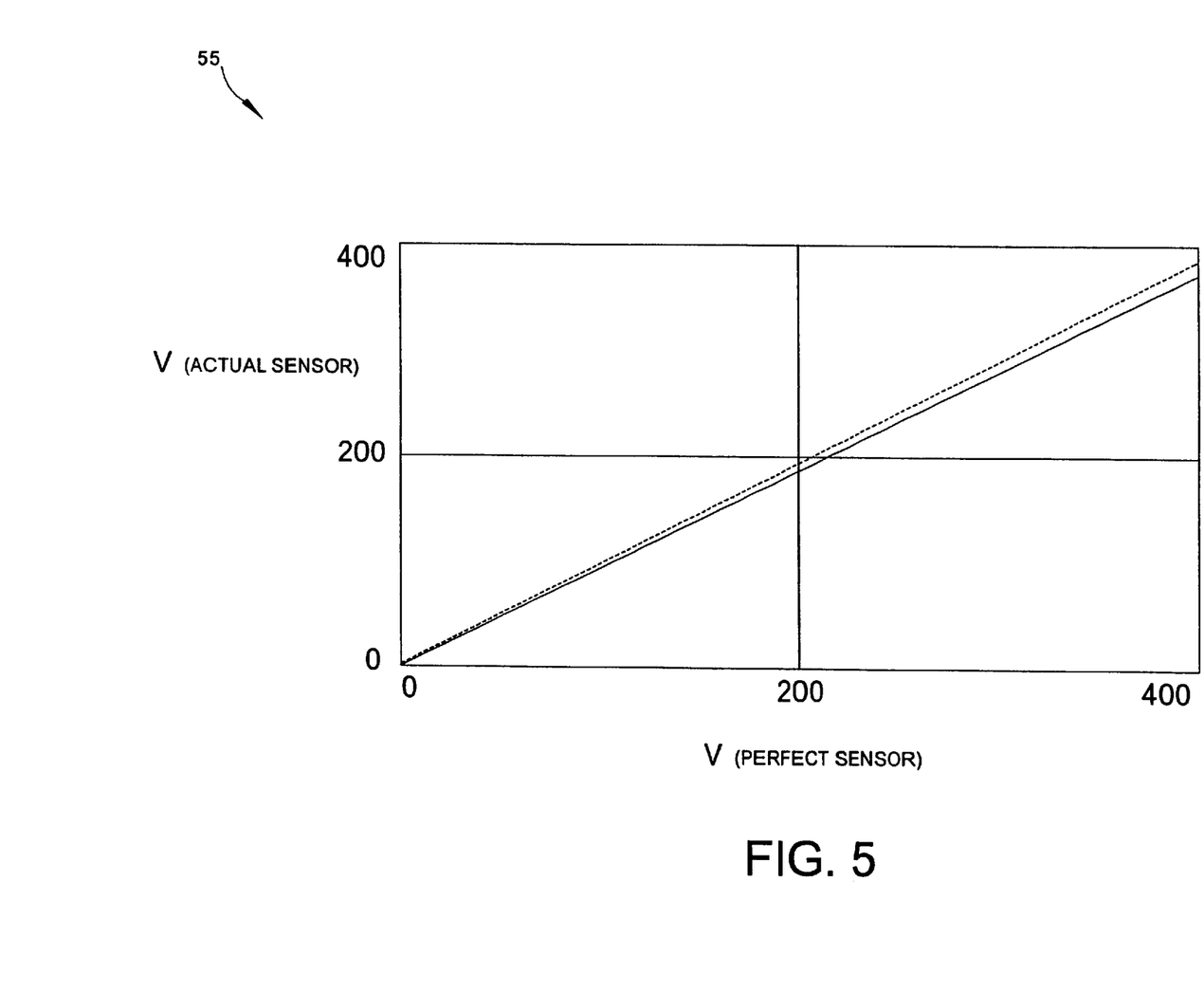
FIG. 5 is a graph of a transfer function of a theoretically perfect sensor and an actual sensor.

To illustrate the operability of portion 10 in optical stabilization of temperature effects on the IR gas analyzer, a linear (linear_$y_i$:=i·0.96) and nonlinear (Nonlinear_$y_i$:= i·0.99) function for a sensor transfer function are compared. Using the linear function as a measurement of perfection, the following will show the errors that can be caused by temperature changes. FIG. 5 illustrates a graph 55 of the linear and non-linear functions. Notably, there is little difference in the two slopes. Nonetheless, this small amount of imperfection can cause a significant error due to changing temperature. Thus, even the best sensor can be improved by the optical method of the preferred embodiment.

Using these two sensor transform functions (linear and nonlinear) it can be seen that for a linear transform function, with a ten (10) unit change in temperature, it can be compared with the same temperature change at any other temperature offset over the full range of temperatures and there is no difference in the two signals. In other words, a ten (10) unit change in temperature is ten (10) units, regardless of the temperature offset. Thus, for example, regardless of whether the temperature changes from 20 to 30 units, or from 380 to 390 units, the OK_RATIO difference (defined below) is still zero because the temperature change (i.e., 10 units) is the same in both cases.

$$OK\_Ratio_x := \frac{linear\_y_x - linear\_y_{X+10}}{linear\_y_{X+offset} - linear\_y_{X+10+offset}} \quad (1)$$

$$OK\_Ratio_1 - OK\_Ratio_{200} = 0 \quad (2)$$

If, however, the nonlinear transfer function is used, the difference over the temperature range is 1.8%. In other words, a ten (10) unit change in temperature can look like a 10.18 unit change in temperature at a different device temperature.

$$Ratio_x = \frac{Nonlinear\_y_x - Nonlinear_{y_{x+10}}}{Nonlinear\_y_{X+offset} - Nonlinear\_y_{X+10+offset}} \quad (3)$$

$$Ratio_1 - Ratio_{200} = 1.827 \cdot \% \quad (4)$$

Now, if the method disclosed herein for using an attenuator (e.g., filter 28) in the optical path is used, this will reduce the energy to the sensor's larger peak data and reduce the 1.8% error down to near zero.

$$FIX\_Ratio_x := \frac{Nonlinear\_y_{x+attenuate} - Nonlinear\_y_{x+10+attenuate}}{Nonlinear\_y_{x+offset} - Nonlinear\_y_{x+10+offset}} \quad (5)$$

$$FIX\_Ratio_1 - FIX\_Ratio_{200} = -0.02332 \cdot \% \quad (6)$$

Figure 6:
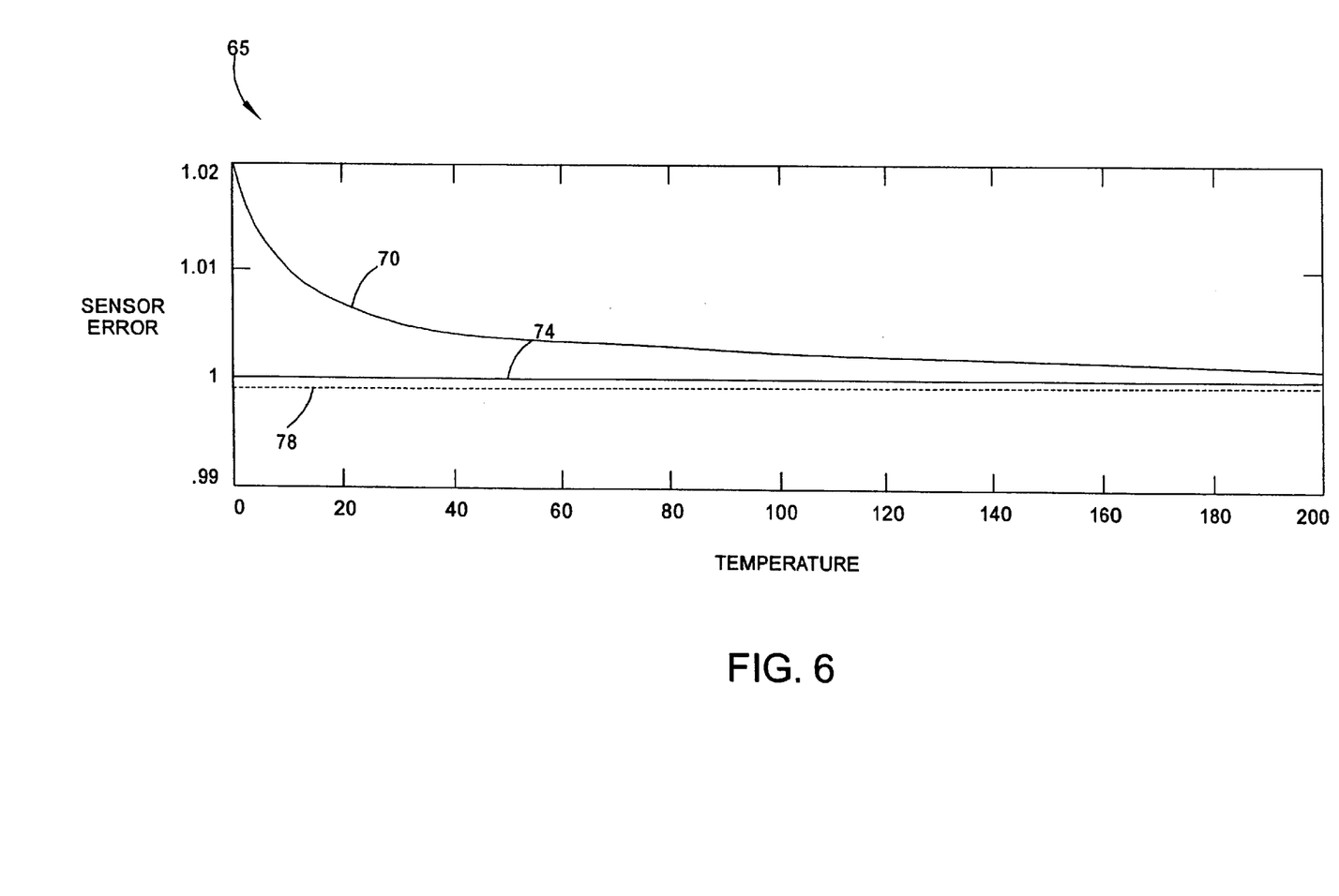
FIG. 6 is a graph of sensor error versus temperature for the transfer function of FIG. 5.

FIG. 6 illustrates a graph 65 showing the full temperature range errors for the equations above. A line 70 represents Ratio$_x$, a line 74 represents OK_Ratio$_x$, and a line 78 represents FIX_Ratio$_x$. Most of the 1.8% error (shown by line 70) could have been calibrated out of the temperature effects using a heater at a high temperature where the error slop is less. However, the warm-up time would be very long to get to that temperature.

Line 74, at the level 1 amount, shows ideal response over the full temperature range and line 78 (almost on top of line 74 ) is the sensor reference gas reading with correction as described herein. Although the correction is not perfect, it is much closer to ideal response then line 70. Advantageously, portion 10 provides reduced gas reading errors over temperature by reducing the sensor's dynamic range requirement. Further, there is reduced sensor noise output by reducing sensor output signal frequency response requirements. The method and apparatus used herein may be used, for example, in a $CO_2$ gas analyzer. In a prototype of such an analyzer, the method according to the preferred embodiment has been tested and performance exceeds the performance of a commercial unit with heaters by a factor of three (3) in stability without needing warm-up to meet the commercial unit specifications. As one of skill in the art would understand, the disclosed method may also be used in analyzers for other gases, such as an anesthetic gas analyzer.

While the embodiments illustrated in the FIGURES and described above are presently preferred, it should be understood that these embodiments are offered by way of example only. Other embodiments may include, for example, different types and variations of gas analyzers. The invention is not limited to a particular embodiment but extends to various modifications, combinations, and permutations that nevertheless fall within the scope and spirit of the appended claims.

What is claimed is:

1. A method of stabilizing temperature effects on a gas analyzer, the method comprising:
    transmitting infrared energy through a plurality of cells in a reference cell drum to a sensor in the gas analyzer, the plurality of cells including at least one cell containing a reference gas and at least one cell containing an air reference;
    interposing a filter in at least one of the plurality of cells in the reference cell drum, wherein energy from the infrared beam is reduced; and
    rotating the reference cell drum such that the infrared energy fully passes through each of the plurality of cells for a limited period of time such that the sensor generates a substantial sine wave signal.

2. The method of claim 1, further comprising matching the filter and the reference gas to provide the sensor with infrared energy at a substantially similar amplitude.

3. The method of claim 1, wherein the step of interposing a filter comprises locating an optical attenuator within at least one cell containing an air reference.

4. The method of claim 1, wherein the step of interposing a filter reduces dynamic range requirements of the sensor, thereby reducing gas reading errors over temperature changes.

5. The method of claim 1, wherein the step of interposing a filter reduces sensor output signal frequency response requirements, thereby reducing sensor noise output.

6. The method of claim 1, wherein the step of transmitting a beam of infrared energy comprises rotating the reference cell drum such that the beam passes through each of the plurality of cells in the reference cell drum one after another.

7. The method of claim 1, wherein the step of interposing a filter comprises interposing a filter in at least one cell containing an air reference.

8. A gas analyzer comprising:
    a source which emits infrared energy;
    a sensor which detects infrared energy emitted from the source;
    a reference cell drum interposed between the source and the sensor, the reference cell drum including a plurality of cells through which the infrared energy passes from the source to the sensor, the plurality of cells including at least one cell containing a reference gas and at least one cell containing an air reference, the reference cell drum further being configured to rotate such that the infrared energy fully passes through each of the plurality of cells for a limited period of time such that the sensor generates a substantial sine wave signal; and
    at least one filter within the at least one cell containing an air reference, the at least one filter providing broad spectrum attenuation to reduce the infrared energy passing through the at least one cell containing an air reference.

9. The gas analyzer of claim 8, wherein the at least one filter and the reference gas are matched to provide the sensor with infrared energy at a substantially similar amplitude.

10. The gas analyzer of claim 8, wherein the sensor is non-linear.

11. The gas analyzer of claim 8, further comprising a gas analyzer environment which has a temperature which varies during operation of the gas analyzer.

12. The gas analyzer of claim 8, wherein the filter comprises an optical attenuator.

13. The gas analyzer of claim 8, wherein the reference gas comprises $CO_2$.

14. The gas analyzer of claim 8, wherein the at least one filter reduces dynamic range requirements of the sensor, thereby reducing gas reading errors over temperature changes.

15. The gas analyzer of claim 8, wherein the at least one filter reduces sensor output signal frequency response requirements, thereby reducing sensor noise output.

16. A gas analyzer which stabilizes temperature effects without using heaters and coolers, the gas analyzer comprising:
    means for transmitting infrared energy through a plurality of cells in a reference cell drum to a sensor, the cells including at least one cell containing a reference gas and at least one cell containing an air reference;
    means for filtering infrared energy passing through the at least one cell in the reference cell drum containing an air reference; and
    means for rotating the reference cell drum such that the infrared energy fully passes through each of the plurality of cells for a limited period of time such that the sensor generates a substantial sine wave signal.

17. The gas analyzer of claim 16, wherein the filtering means is chosen based on the reference gas such that infrared energy passing through the at least one cell containing the gas reference will have substantially the same amplitude as the infrared energy passing through the at least one cell containing the air reference.

18. The gas analyzer of claim 16, wherein the sensor is non-linear.

19. The gas analyzer of claim 16, further comprising a gas analyzer environment which has a temperature which varies during operation of the gas analyzer.

20. The gas analyzer of claim 16, wherein the reference gas comprises an anesthetic gas.

* * * * *

UNITED STATES PATENT AND TRADEMARK OFFICE
CERTIFICATE OF CORRECTION

PATENT NO. : 6,359,278 B1  Page 1 of 1
DATED : March 19, 2002
INVENTOR(S) : James E. Graham It is certified that error appears in the above-identified patent and that said Letters Patent is hereby corrected as shown below:

Column 4,
Equation 3, first line before "$y_{x+100}$", insert -- _ --.

Column 5,
Line 9, delete space between "74" and ")".
Line 11, insert a paragraph before "Advantageously,".

Signed and Sealed this

Fourth Day of June, 2002

*Attest:*

*Attesting Officer*

JAMES E. ROGAN
*Director of the United States Patent and Trademark Office*